United States Patent [19]

Butz et al.

[11] 4,292,273

[45] Sep. 29, 1981

[54] RADIOIMMUNOASSAY PLATE

[75] Inventors: David E. Butz, Littleton; Pasquale L. Pepicelli, Chelmsford, both of Mass.

[73] Assignee: Data Packaging Corporation, Cambridge, Mass.

[21] Appl. No.: 53,260

[22] Filed: Jun. 29, 1979

[51] Int. Cl.³ .............................................. C12M 1/20
[52] U.S. Cl. .................................. 422/102; 422/104; 435/301; 435/298; 220/23.6
[58] Field of Search ............... 435/301, 287, 291, 298, 435/300, 810; 422/102, 104, 61, 99; 206/564; 220/23.6, 23.8

[56] References Cited

U.S. PATENT DOCUMENTS

| | | | |
|---|---|---|---|
| 3,597,326 | 8/1971 | Liner | 220/23.6 |
| 4,010,078 | 3/1977 | Taylor | 435/301 |
| 4,038,149 | 7/1977 | Liner et al. | 422/102 |
| 4,154,795 | 5/1975 | Thorne | 422/102 |

*Primary Examiner*—Benoit Castel
*Attorney, Agent, or Firm*—Wolf, Greenfield & Sacks

[57] ABSTRACT

A radioimmunoassay plate composed of a tray and a cover. The tray has a plurality of wells having downwardly tapered side walls and coplanar bottom walls. Each bottom wall has a flat central portion and rounded peripheral portion, the peripheral portion merging into the side wall.

8 Claims, 6 Drawing Figures

RADIOIMMUNOASSAY PLATE

INTRODUCTION

This invention relates to culture plates used in the laboratory and more particularly comprises a new and improved radioimmunoassay plate. These plates are typically used for cloning specific antibodies.

Radioimmunoassay plates (R I A plates) have a plurality of wells in which the culture growth occurs. The R I A plates now available have wells with either flat or round bottoms, and each has specific disadvantages. The flat bottom wells have a tendency to dome so as to create a ring of the culture material around the periphery of the bottom wall. This ring frequently creates a halo image on the film exposed to the plate, and the image may merge with the images of adjacent wells. On the other hand, the round bottom wells have essentially point contact with the film on which the plates are placed, and at best this provides minimum quantities of the material in close proximity with the film at each well. And if the plate is at all warped, contact is lost altogether.

The principle object of the present invention is to provide a radioimmunoassay plate having a well bottom wall configuration which promotes proper contact with film on which the plate is to be exposed.

Another object of the present invention is to provide an R I A plate that has stacking facilities so as to enable a number of plates to be stacked on top of one another without tipping or sliding sideways.

To accomplish these and other objects, the R I A plate of this invention comprises a bottom plate or tray and cover. The tray has a plurality of wells having bottom walls that are flat in the central portion and rounded at the periphery so as to merge into the side walls of the wells. The diameter of the flat central portion of the bottom wall of each well is approximately ½ the total diameter of the well. This configuration prevents doming of the bottom wall and the formation of non-concentrated areas to create halo images on the film on which the plate is exposed. The flat bottom configuration also assures proper contact between the bottom wall of each well and the film.

The cover is provided with a seat about its periphery to support the side wall of a tray placed above it so that the tray will not slide or tilt on the cover.

These and other objects and features of the present invention will be better understood and appreciated from the following detailed description of one embodiment thereof, selected for purposes of illustration and shown in the accompanying drawings.

BRIEF FIGURE DESCRIPTION

DETAILED DESCRIPTION

Radioimmunoassay plates are ordinarily used as follows:

Cells are deposited in each of the wells and are incubated for a selected period. To determine whether cell growth has occurred in the wells, radioactive labeling material is deposited in each well. The labeling material is absorbed in the wells where growth has taken place. The radioactive material which has not been absorbed is then washed from each of the wells. The plate is next placed on film to photographically determine in which wells the radioactive material has been absorbed by the cells. In order to accurately determine by the photographic process which cells have absorbed the radioactive material, good contact must occur between the well bottom walls and the film.

In accordance with the present invention the R I A plates include a tray 10 and cover 12. Both are made of plastic material such as inexpensive styrene or vinyl and may be transparent. They are formed typically by the vacuum or pressure forming process, so that they may be made rapidly and in large numbers at low cost.

Figure 4:
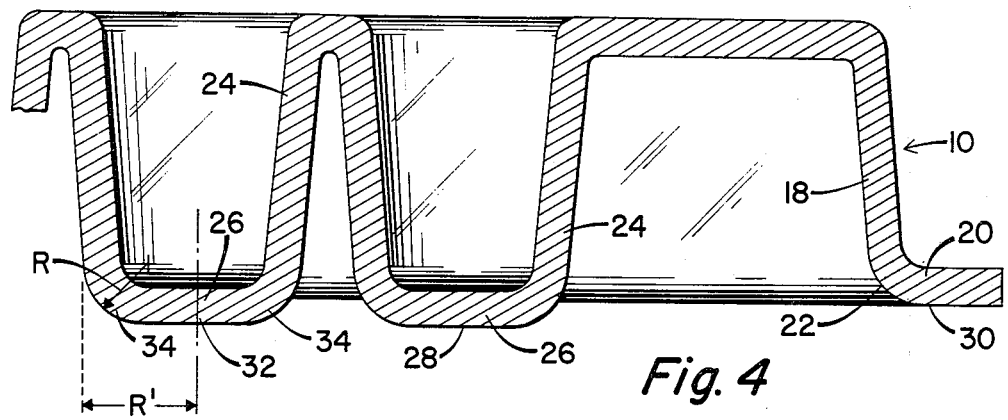
FIG. 4 is an enlarged fragmentary cross sectional view of the wells of the tray taken along the section line 4—4 in FIG. 2.
Figure 5:
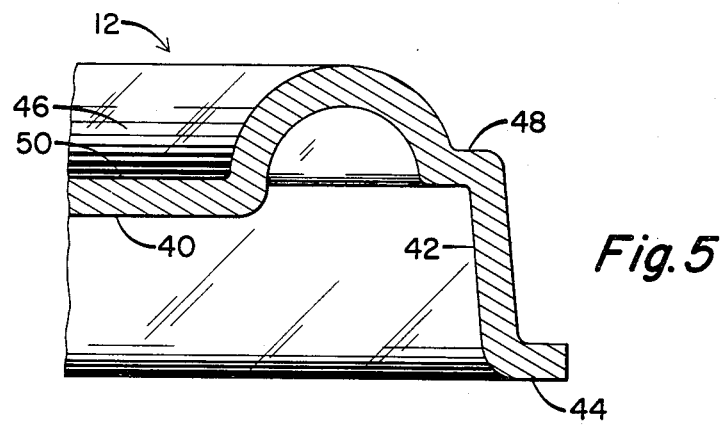
FIG. 5 is an enlarged fragmentary cross sectional view of the cover taken along section line 5—5 of FIG. 3.

The tray 10 includes a horizontal wall 14 from which a number of wells 16 depend and a peripheral side wall 18 which terminates at its lower end in a horizontal flange or lip 20. In the embodiment shown, 96 wells are formed in the tray 10, and the overall plan dimensions of the plate are approximately 3⅜ by 5 inches. The wall thickness is approximately 0.025 inch and is generally uniform throughout. Peripheral side wall 18 is slightly flared in a downward direction at approximately a 2° angle with the vertical and is joined at a radius 22 to the lip 20 (see FIG. 4).

Each well is formed by a downwardly tapered side wall 24 and a bottom wall 26. The lower surface 28 of each bottom wall lies below the plane of the bottom surface 30 of lip 20, and the bottom walls of all the wells are coplanar. The side walls 24 are circular in cross-section, and the taper is approximately 5° to the vertical. The taper of the peripheral side wall 18 and the tapered side walls 24 of the wells enable the tray 10 to be readily stripped from the mold after forming.

The well bottom wall 26 is composed of a flat central portion 32 and a rounded peripheral portion 34 that smoothly merges with the side wall 24. The radius R of the corners 34 is substantially equal to ½ the total radius R' of the bottom wall 32. In the embodiment shown, the inner diameter of each well at the top wall 14 is approximately 0.300 inch.

Figure 1:
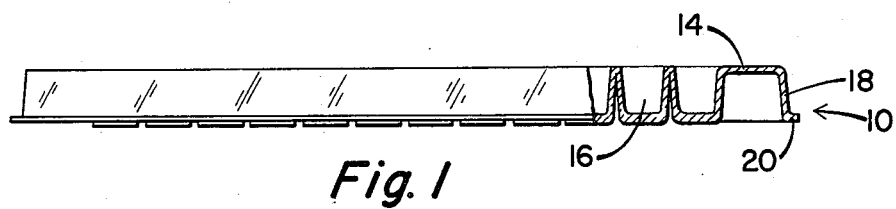
FIG. 1 is a side view, partly in section, of the tray of an R I A plate constructed in accordance with this invention.
Figure 2:
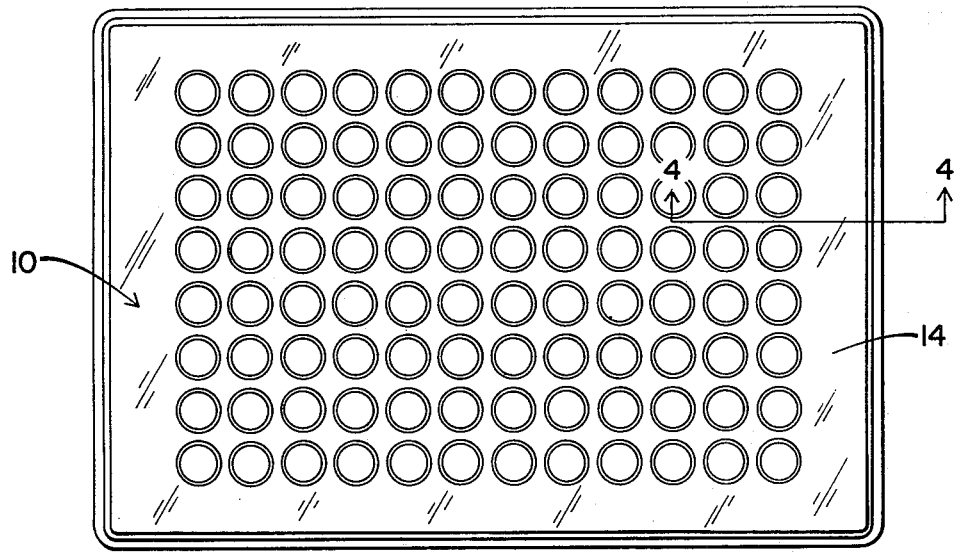
FIG. 2 is a top plan view of the tray.
Figure 3:
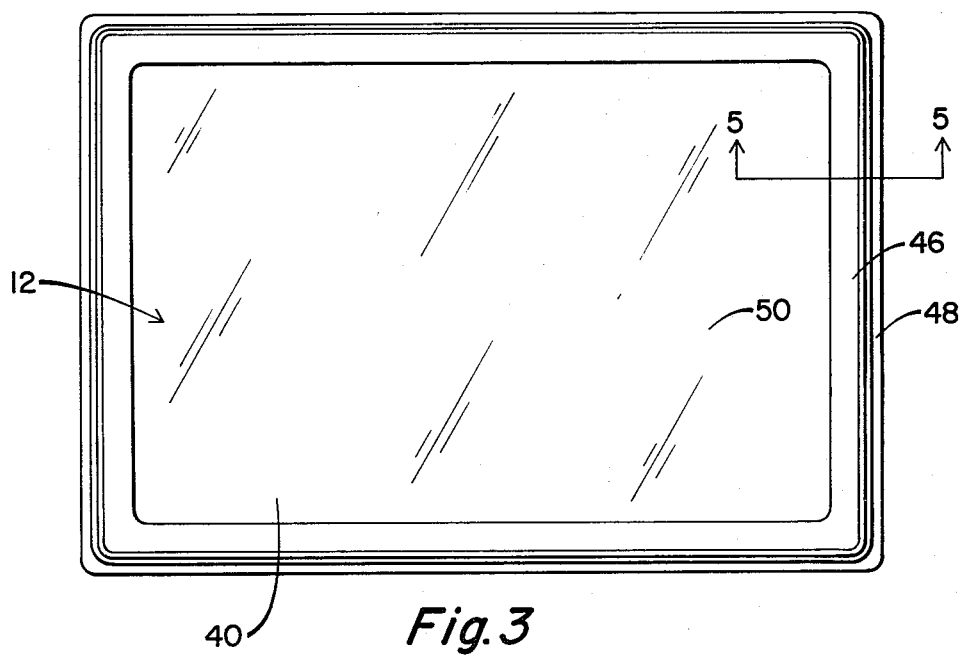
FIG. 3 is a top plan view of the cover of the R I A plate.

Cover 12 includes a top wall 40 and a peripheral skirt 42 that flares downwardly at an angle of approximately 2° with the vertical. The cover also includes a lip 44 about its full periphery which extends horizontally outward from the bottom of the skirt. A bead 46 is formed at the periphery of top wall 40 just inwardly of skirt 42 leaving a narrow shoulder 48 at the top of the skirt, which may support the tray of an R I A plate stacked above it, as explained in detail below. The upper surface of the shoulder 48 is disposed above the plane of the upper surface 50 of top wall 40 within bead 46 so as to prevent the bottom walls 32 of the wells from interfering with the stacking of the tray disposed on shoulder 48. The bead 46 and shoulder 48 are provided on all four sides of the cover as is shown in FIG. 3.

Figure 6:
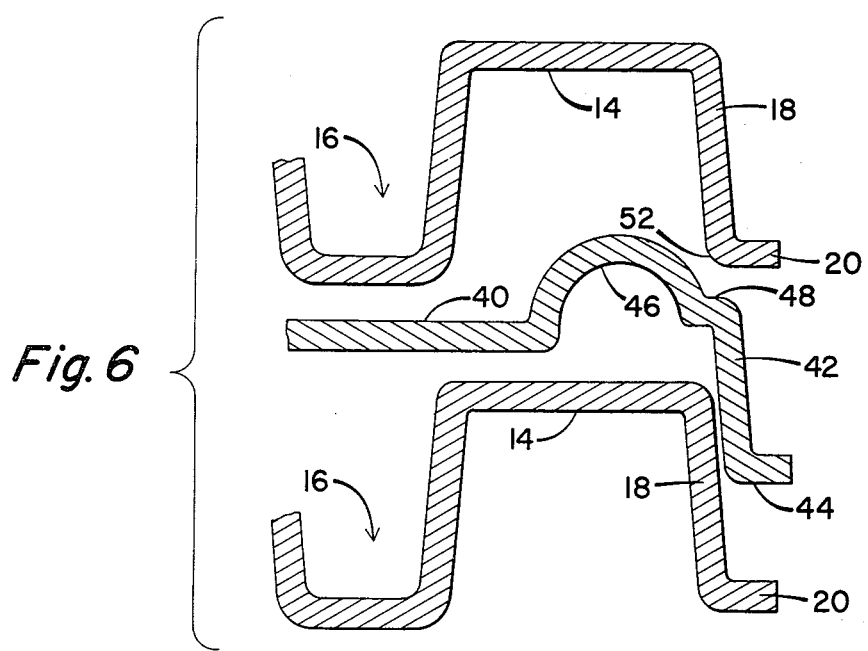
FIG. 6 is a fragmentary cross sectional view suggesting the manner in which the cover fits on the tray below as well as the way a tray may stack on top of the cover.

In FIG. 6 the manner in which the cover closes the tray as well as the manner in which the R I A plates may be stacked one upon another is shown. When the cover 12 is placed on the tray to close it, cover skirt 42 forms a surface to surface seal with side wall 18 of the tray, and the horizontal wall 40 of the cover overlies the wells 16. The wall 40 may or may not contact the horizontal wall 14 of the tray, but it is not intended that the wall 40 separately seal the several wells from one another. When the cover closes the tray, the lips 20 and 44 of the tray and cover, respectively are spaced apart a sufficient distance so that they may be grasped to remove the cover from the tray.

Shoulder 48 is shown to provide a convenient seat for the inner edge of the lip 20 of the tray 10 placed above it. The inner corner 52 of lip 20 engages the outer side of bead 46 so that the tray 10 cannot easily slide laterally on the cover. Thus, stability is created in the stack so as to prevent the R I A plates from tumbling or tilting in a manner which could disturb their contents. And because the shoulder 48 is disposed above the plane of the horizontal wall 40, the bottoms 32 of the wells do not interfere with proper seating of the lips 20 on the shoulders. The upper surface of shoulder 48 may be 0.030 inch above the plane of the upper surface 50, while the lower surface of lip 20 may be 0.030 inch above the bottom surface of wall 32.

The configuration of the bottom wall 32 of each well provides several advantages over the prior art. Because each well bottom wall has a substantial area that is flat, a substantial amount of material contained in the well will be in close proximity with the film on which the bottom plate is placed and exposed. The radius about the periphery eliminates the crowning problem which frequently occurs when the corners joining the side and bottom walls of the well are substantially square. And while a substantial area is provided for contact between the bottom wall and the film, the surface is not so great as to spread the material in the well too thinly or concentrate the material at the periphery, which in turn causes a halo image to be formed on the film. As mentioned in the introduction, that halo image can merge with similar images from other wells if the problem is particularly acute so as to make it difficult or impossible to detect all growth. The flat areas in each well also assure that there is contact between the bottom wall of each well and the film. It will be appreciated that with R I A plates having round well bottom walls, any warping of the tray will cause the normal point contact between the well bottom and the film to be interrupted.

From the foregoing description those skilled in the art will appreciate that modifications may be made of this invention without departing from its spirit. Therefore, it is not intended to limit the scope of this invention to the embodiment illustrated and described. Rather, it is intended that the scope of this invention be determined by the appended claims and their equivalents.

What is claimed is:

1. A radioimmunoassay plate comprising:
    a bottom tray made of transparent material and having a plurality of wells extending downwardly from its top plane with the wells defined by downwardly tapered side walls and a bottom wall, said bottom walls lying in a common plane parallel to the top plane of the tray,
    a peripheral side wall extending downwardly from the top plane and terminating at its lower edge above the plane of the bottom walls, whereby the bottom walls may all contact a planar surface on which the tray is placed without interference from the peripheral side walls,
    each of said well bottom walls being flat at its central portion and having a substantial radius at the junction of the bottom and side wall equal to approximately half the radius of the bottom wall,
    a removable cover for the bottom tray having a top wall which is adapted to closely overlie the top plane of the tray and having a skirt which engages and is supported by the peripheral side wall of the tray and forms a seal therewith when positioned to cover the tray and the wells in it,
    an outwardly extending flange formed at the bottom of the peripheral side wall of the tray,
    a seat formed in the cover for receiving the flange of a second bottom tray stacked on it to support the second tray on the cover,
    and means provided in the cover for preventing a second bottom tray stacked on it from sliding sideways off the cover.

2. A radioimmunoassay plate as defined in claim 1 further characterized by
    an outwardly extending flange formed at the bottom of the skirt of the cover,
    said side wall and skirt forming a surface to surface seal with the flanges separated when the cover is in place on the tray, said flanges facilitating removal of the cover from the tray.

3. A radioimmunoassay plate comprising:
    a tray having a plurality of wells for receiving material and each defined by a downwardly extending side wall and a bottom wall;
    said bottom walls having coplanar flat, central portions and rounded peripheral portions which merge smoothly into the side walls for preventing the material from forming a halo image on film exposed against the bottom walls while enabling all the bottom walls to make surface to surface contact on a planar sheet of film on which the tray is placed,
    said tray having a peripheral side wall with the lowermost portion of the side wall disposed above the flat central portions of the bottom walls of the wells so as not to interfere with said contact of the flat central portions with the sheet of film,
    the flat central portion of each of the well bottom walls being approximately half the diameter of the well measured to the side wall,
    a cover removably mounted on the tray and having a top wall that overlies the top of the wells when the cover is mounted on the tray,
    said cover having a skirt extending downwardly from the top wall for engaging and forming a seal with the tray to close the wells to ambient atmosphere,
    and means provided in the cover for supporting a second tray stacked on it identical to the tray covered by it.

4. A radioimmunoassay plate as defined in claim 3 further characterized by
    said means in the cover including a shoulder at the periphery of the cover for receiving the bottom edge of the peripheral side wall of the second tray,
    a bead formed in the cover inwardly of the shoulder to engage the inside surface of the peripheral side wall to prevent the second tray from moving laterally on the cover, and a recess in the top wall radially inside the bead and in a place spaced below the plane of the shoulder so as not to engage the bottoms of the wells of the second tray and interfere with the seating of the peripheral wall of the second tray on said shoulder.

5. A radioimmunoassay plate as defined in claim 3 further characterized by
said well side walls tapering in a downwardly direction.

6. A radioimmunoassay plate as defined in claim 3 further characterized by
said well side walls being circular in cross section.

7. A radioimmunoassay plate as defined in claim 6 further characterized by
said cover skirt engaging the peripheral side wall of the tray to form the seal with the tray.

8. A radioimmunoassay plate as defined in claim 3 wherein the tray is transparent.

* * * * *